United States Patent
Chaudhari et al.

Patent Number: 6,093,847
Date of Patent: Jul. 25, 2000

[54] PROCESS FOR THE PREPARATION OF IBUPROFEN

[75] Inventors: Raghunath V. Chaudhari; Seayad A. Majeed; Jayasree Seayad, all of Maharashtra, India

[73] Assignee: Council of Scientific and Industrial Research, New Delhi, India

[21] Appl. No.: 09/281,928

[22] Filed: Mar. 31, 1999

[30] Foreign Application Priority Data

Dec. 9, 1998 [IN] India .................... 3697/Del/98

[51] Int. Cl.⁷ .................................... C07C 51/10
[52] U.S. Cl. .................................... 562/406
[58] Field of Search .......................... 562/406

[56] References Cited

U.S. PATENT DOCUMENTS

| | | | |
|---|---|---|---|
| 4,843,172 | 6/1989 | Tanaka et al. | 562/406 |
| 5,055,611 | 10/1991 | Lin et al. | 562/406 |
| 5,166,418 | 11/1992 | Hendricks et al. | 562/406 |
| 5,278,335 | 1/1994 | Chockaingam | 560/105 |

*Primary Examiner*—Michael P. Woodward
*Assistant Examiner*—Sherif A. Kafafi
*Attorney, Agent, or Firm*—Birch, Stewart, Kolasch & Birch, LLP

[57] ABSTRACT

The present invention relates to an process for the preparation of ibuprofen, which comprises reacting para isobutyl phenylethanol (p-IBPE), a halide source, a protonic acid, water and the catalyst which is a compound having formula 1 which is shown herebelow:

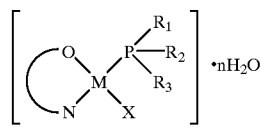

Formula I

Wherein
M = a group VIII metal specifically palladium or platinum, $R_1, R_2, R_3$ = substituents on the phosphine ligand such as hydrogen, alkyl, aryl, arylalkyl cycloaliphatic, X = groups such as aryl or alkyl sulphonato or aryl or alkyl carboxylato ort formato or halides such as $Cl^-$, $Br^-$, $I^-$,

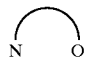

= a semilabile anionic chelating ligand containing a donor and an $O^-$ group such as 8-hydroxy quinoline, 2-hydroxy pyridine, 2-(2-hydroxy ethyl)pyridine, pyridyl-2-, piperidyl-2-, quinolyl-2-, isoquinolyl-1- and isoquinolyl-3- carboxylates, particularly pyridyl-2-carboxylate, piperidyl-2-carboxylate, and 8-hydroxyquinoline, $1 < n < 10$ in an organic solvent under constant stirring in carbon monoxide atmosphere under biphasic or homogeneous conditions, at a temperature ranging between 30 to 130° C., for a period ranging between 0.3 to 6 hrs, at pressure ranging between 50 to 1500 psig, cooling the reaction mixture to ambient temperature, flushing the reaction vessel with inert gas, removing the solvent by conventional methods, separating the catalyst and isolating the product.

28 Claims, 1 Drawing Sheet

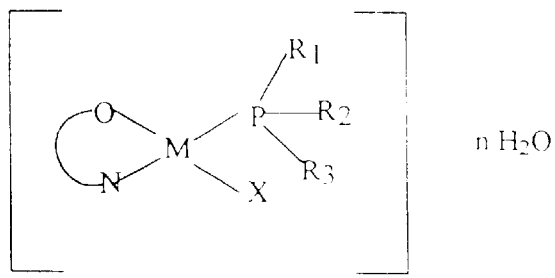

Formula I

Wherein

| | |
|---|---|
| M | = a group VIII metal specifically palladium or platinum |
| $R_1, R_2, R_3$ | = substituents on the phosphine ligand such as hydrogen, alkyl, aryl, arylalkyl cycloaliphatic |
| X | = groups such as aryl or alkyl sulphonato or aryl or alkyl carboxylato or formato or halides such as $Cl^-$, $Br^-$, $I^-$ |

= a semilabile anionic chelating ligand containing a N donar and an $O^-$ group such as 8-hydroxy quinoline, 2-hydroxy pyridine, 2-(2-hydroxy ethyl)pyridine, pyridyl-2-, piperidyl-2-, quinolyl- 2-, isoquinolyl-1- and isoquinolyl-3- carboxylates, particulaly pyridyl-2-carboxylate, piperidyl-2 carboxylate, and 8-hydroxyquinoline $1 \leq n < 10$

PROCESS FOR THE PREPARATION OF IBUPROFEN

FIELD OF THE INVENTION

This invention relates to an improved process for the preparation of ibuprofen. More particularly this invention relates to the improved process for conversion of para-isobutyl-phenyl-ethanol (p-IBPE) to ibuprofen, using a catalyst having the general formula I, containing a semilabile anionic chelating ligand, which is an organic compound containing a N donor and an O⁻ group.

BACKGROUND

Ibuprofen is a well known anti-inflammatory drug. The conventional synthesis of ibuprofen involves six steps which use hazardous chemicals like sodium cyanide and the waste materials produced require downstream treatments for disposal. Recently, Hoechst Celanese Corporation developed a novel, environmentally benign, three step catalytic route for the synthesis of ibuprofen, in which carbonylation of para isobutyl phenyl ethanol is the key step. In the processes described in patented literature, the catalysts used were mainly Pd(PPh$_3$)$_2$Cl$_2$ or PdCl$_2$ or Pd(OAc)$_2$ along with excess phosphine ligands (EP 0,400,892A3, EP 0,284, 310A1), which gave lower reactions rates (TOF=25–35 h$^{-1}$) and lower selectivity to ibuprofen (56–69%) under mild conditions (130° C., 1000 psig). Higher selectivity (>95%) was obtained only at very high pressures of 2000 to 4500 psig and the rates still remained low. U.S. Pat. No. 5,536,874 and the publication J. Chem. Tech. Biotechnol, 1997, 70, 83–91, describe the carbonylation of p-IBPE in a two-phase system wherein one phase is an aqueous medium which contains a water soluble palladium complex and an acid promoter. These processes also have disadvantages such as low reaction rates (TOF=0.1 to 0.4 h$^{-1}$) and lower ibuprofen selectivity (59–74%) under mild reaction conditions (90° C., 450 to 900 psig).

The object of the present invention, therefore, is to provide an improved process for the preparation of ibuprofen by carbonylation of para isobutyl phenyl ethanol.

SUMMARY OF THE INVENTION

The inventors of the present invention have observed that the use of a new transition metal complex having general formula I in the drawing accompanying this specification (which contains a semilabile anionic chelating ligand which is an organic compound containing a N donor and an O⁻ group) provides an improved catalyst for the carbonylation of para-isobutyl-phenyl-ethanol (p-IBPE) to ibuprofen. The use of such a catalyst gives high reaction rates and high ibuprofen selectivity under mild reaction conditions.

BRIEF DESCRIPTION OF THE ACCOMPANYING DRAWING

FIG. 1 represents the structural formula of the catalyst employed in the improved process.

DETAILED DESCRIPTION OF THE INVENTION

According the present invention provides all improved process for the preparation of ibuprofen, which comprises reacting para-isobutyl-phenylethanol (p-IBPE), a halide source, a protonic acid, water and a catalyst having formula I which is shown herebelow:

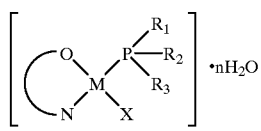

Formula I

Wherein
M = a group VIII metal specifically palladium or platinum,
R$_1$, R$_2$, R$_3$ = substituents on the phosphine ligand such as hydrogen, alkyl, aryl, arylalkyl cycloaliphatic,
X = groups such as aryl or alkyl sulphonato or aryl or alkyl carboxylato ort formato or halides such as Cl⁻, Br⁻, I⁻,

= a semilabile anionic chelating ligand containing a donor and an O⁻group such as 8-hydroxy quinoline, 2-hydroxy pyridine, 2-(2-hydroxy ethyl)pyridine, pyridyl-2-, piperidyl-2-, quinolyl-2-, isoquinolyl-1- and isoquinolyl-3- carboxylates, particularly pyridyl-2-carboxylate, piperidyl-2 carboxylate, and 8-hydroxyquinoline, 1<n<10
in an organic solvent under stirring in a carbon monoxide atmosphere under biphasic or homogenous conditions, at a temperature ranging between 30 to 130° C. for a period ranging between 0.3 to 6 hrs, at pressures ranging between 50 to 1500 psig, cooling the reaction mixture to ambient temperature, flushing the reaction vessel with inert gas, removing the solvent by conventional methods, separating the catalyst and isolating the product.

In the preferred catalyst M=Pd; R$_1$, R$_2$, R$_3$=Phenyl; X=p-toluenesulphonato(OTs); N, O⁻=pyridyl-2-carboxylate; n=3.

The catalyst employed in the present improved process and the process for the synthesis of the said catalyst are described in detail in the co-pending Indian Patent Application No. 3698/Del/98 filed on Dec. 9, 1998 (corresponding U.S. application Ser. No. 09/281,929 dated Mar. 31, 1999.)

In another embodiment, the halide source may be any of the halide salts such as lithium chloride, sodium chloride, potassium chloride, lithium iodide, lithium bromide, sodium bromide, sodium iodide, potassium bromide, potassium iodide, tetrabutyl ammonium chloride, tetrabutyl ammonium bromide and tetrabutyl ammonium iodide or hydro halic acids such as hydrochloric acid, hydrobromic acid and hydro iodic acid.

In yet another embodiment, the protonic acid used may be any of the hydro halic acids such as hydrochloric acid, hydrobromic acid and hydro iodic acid or other protonic acids such as para-toluene sulphonic acid, methane sulphonic acid, trifluoromethane sulphonic acid, formic acid, oxalic acid, acetic acid and trifluoro acetic acid.

In yet another embodiment, the organic solvent may be aromatic hydrocarbons like, benzene, toluene, xylenes, or ketones like methyl-ethyl ketone, acetone or cyclic ethers such as tetrahydrofuran, dioxan, or nitriles such as acetonitrile or amides like N-methyl pyrrolidone.

In another embodiment, the concentration of the catalyst may be one mole of catalyst for every 50 to 50000 moles of p-IBPE, preferably 1 mole of catalyst for every 100 to 6000 moles of p-IBPE and more preferably one mole of catalyst for every 150 to 2000 moles of p-IBPE.

In still another embodiment, the amount of halide source per gram mole of catalyst may be in the range of 5 to 500 moles, preferably 20 to 300 moles, and more preferably 50 to 150 moles.

In another embodiment, the amount of acid source per gram mole of catalyst may be in the range of 5 to 500 moles, preferably 20 to 300 moles, and more preferably 50 to 150 moles.

In a feature of the invention, the reaction can be conveniently carried out in a stirred reactor with the improved catalyst employed with a suitable solvent in presence of carbon monoxide.

In another feature of the invention, the reaction can be carried out even at low pressures of carbon monoxide (up to 50 psig).

In yet another feature of the invention, the reaction can be carried out in a biphasic medium as well as homogeneous medium.

In another feature of the invention, the reaction in the homogeneous medium provides further improvement than the reaction in biphasic medium.

In another feature of the invention, considerable enhancement in reaction rate is achieved at higher p-IBPE concentrations.

In yet another feature of the invention, excess of product does not lower further reaction rate and selectivity so that recycling of the catalyst can be carried out even in the presence of the product.

In another feature of the invention, there is no need of excess ligands for the reaction.

In still another feature the invention, the catalyst used in the improved process is stable even in the absence of excess ligands and can be recycled efficiently.

The improved process of the present invention is described herein below with examples, which are illustrative only and should not be construed to limit the scope of the present invention in any manner.

EXAMPLE 1

A 50 ml stirred autoclave was charged with the following reactants
ρ-IBPE: 0.01685 mol
Catalyst having formula I: $1.48 \times 10^{-4}$ mol
10% HCl: 6 ml
Methyl ethyl ketone: 16 ml The contents of the autoclave were flushed with nitrogen and then many times with carbon monoxide. Thereafter, the contents were heated to 115° C. After the temperature is attained, the autoclave was pressurized to 1000 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analysed by gas chromatography (GC). The GC analysis showed TOF of 25 $h^{-1}$ and 87% conversion of p-IBPE with ibuprofen selectivity of 86% and n/iso ratio of 0.09. The product was then isolated after removing the catalyst which was precipitated by adding hexane, and evaporating the solvent.

EXAMPLE 2

A 50 ml stirred autoclave was charged with the following reactants
ρ-IBPE: 0.01685 mol
Catalyst having formula I: $1.48 \times 10^{-4}$ mol
p-toluene sulphonic.acid : 0.0163 mol
LiCl: 0.0163 mol
H$_2$O: 6 ml
Methyl ethyl ketone: 16 ml The contents of the autoclave were flushed with nitrogen and then many times with carbon monoxide. Thereafter, the contents were heated to 115° C. After the temperature is attained, the autoclave was pressurized to 1000 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analysed by gas chromatography.

The GC analysis showed TOF of 200 $h^{-1}$ and 98% conversion of p-IBPE with ibuprofen selectivity of 83% and n/iso ratio of 0.14. The product was then isolated after removing the catalyst which was precipitated by adding hexane, and evaporating the solvent.

TABLE 1

| Example | System | ρ-IBPE conversion, % | Ibuprofen selectivity, % | n/iso | TOF, $h^{-1}$ |
| --- | --- | --- | --- | --- | --- |
| 1 | HCl | 87 | 86 | 0.09 | 25 |
| 2 | LiCl/p-tsa | 98 | 83 | 0.14 | 200 |

EXAMPLE 3

A 50 ml stirred autoclave was charged with the following reactants
ρ-IBPE: 0.01685 mol
Catalyst having formula I: $1.4125 \times 10^{-4}$ mol
p-toluene sulphonic acid : 0.0163 mol
LiCl: 0.0163 mol
H$_2$O: 40000 ppm
Methyl ethyl ketone: 16 ml The contents of the autoclave were flushed with nitrogen and then many times with carbon monoxide. Thereafter, the contents were heated to 115° C. After the temperature is attained, the autoclave was pressurized to 1000 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the final reaction mixture analysed by gas chromatography.

The GC analysis showed TOF of 270 $h^{-1}$ and 97.8% conversion of p-IBPE with ibuprofen selectivity of 98% and n/iso ratio of 0.0206.

EXAMPLE 4

A 50 ml stirred autoclave was charged with the following reactants
Final reaction mixture of Example 3
ρ-IBPE: 0.01685 mol
$H_2O$: 30000 ppm The contents of the autoclave were flushed with nitrogen and then many times with carbon monoxide. Thereafter, the contents were heated to 115° C. After the temperature is attained, the autoclave was pressurized to 1000 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the final reaction mixture analysed by gas chromatography.

The GC analysis showed TOF of 265 $h^{-1}$ and 97.8% conversion of p-IBPE with ibuprofen selectivity of 97% and n/iso ratio of 0.01546. The product was then isolated after removing the catalyst which was precipitated by adding hexane, and evaporating the solvent.

TABLE 2

| Example | Medium | ρ-IBPE conversion, % | Ibuprofen selectivity, % | n/iso | TOF, $h^{-1}$ |
|---|---|---|---|---|---|
| 2 | Biphasic | 98 | 83.00 | 0.140 | 200 |
| 3 | Homogeneous | 98 | 96.50 | 0.029 | 275 |

TABLE 3

| Example | ρ-IBPE concentration, mol | ρ-IBPE conversion, % | Ibuprofen selectivity, % | n/iso | TOF, $h^{-1}$ |
|---|---|---|---|---|---|
| 3 | 0.01685 | 97.8 | 98 | 0.01546 | 275 |
| 4 | 0.01685 (recycle of 3) | 97.8 | 97 | 0.0206 | 265 |
| 5 | 0.05618 | 98 | 96.5 | 0.029 | 640 |

EXAMPLE 5

A 50 ml stirred autoclave was charged with the following reactants
ρ-IBPE: 0.05618 mol
Catalyst having formula I: 1.4125 × $10^{-4}$ mol
p-toluene sulphonic acid : 0.0163 mol
LiCl: 0.0163 mol
$H_2O$: 60000 ppm
Methyl ethyl ketone: 16 ml The contents of the autoclave were flushed with nitrogen and then many times with carbon monoxide. Thereafter, the contents were heated to 115° C. After the temperature is attained, the autoclave was pressurized to 1000 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the final reaction mixture analysed by gas chromatography.

The GC analysis showed TOF of 640 $h^{-1}$ and 98% conversion of p-IBPE with ibuprofen selectivity of 96.5% and n/iso ratio of 0.029. The product was then isolated after removing the catalyst which was precipitated by adding hexane, and evaporating the solvent.

EXAMPLE 6

A 50 ml stirred autoclave was charged with the following reactants
ρ-IBPE: 0.05618 mol
Catalyst having formula I: 1.4125 × $10^{-4}$ mol
p-toluene sulphonic acid : 0.0163 mol
LiCl: 0.0163 mol
$H_2O$: 60000 ppm
Methyl ethyl pyrrolidone: 16 ml The contents of the autoclave were flushed with nitrogen and then many times with carbon monoxide. Thereafter, the contents were heated to 115° C. After the temperature is attained, the autoclave was pressurized to 1000 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the final reaction mixture analysed by gas chromatography.

The GC analysis showed TOF of 212 $h^{-1}$ and 96% conversion of p-IBPE with ibuprofen selectivity of 97.3% and n/iso ratio of 0.018. The product was then isolated after removing the catalyst which was precipitated by adding hexane, and evaporating the solvent.

EXAMPLE 7

A 50 ml stirred autoclave was charged with the following reactants
ρ-IBPE: 0.05618 mol
Catalyst having formula I: 1.4125 × $10^{-4}$ mol
p-toluene sulphonic acid : 0.0163 mol
LiCl: 0.0163 mol
$H_2O$: 50000 ppm
Tetrahydrofuran: 16 ml The contents of the autoclave were flushed with nitrogen and then many times with carbon monoxide. Thereafter, the contents were heated to 115° C. After the temperature is attained, the autoclave was pressurized to 1000 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the final reaction mixture analysed by gas chromatography.

The GC analysis showed TOF 574 $h^{-1}$ and 98% conversion of p-IBPE with ibuprofen selectivity of 94.78% and n/iso ratio dot 0.049. The product was then isolated after removing the catalyst which was precipitated by adding hexane, and evaporatinig the solvent.

TABLE 4

| Example | Solvent | p-IBPE conversion, % | Ibuprofen selectivity, % | n/iso | TOF, $h^{-1}$ |
|---|---|---|---|---|---|
| 5 | MEK | 98 | 96.50 | 0.029 | 640 |
| 6 | NMP | 96 | 97.30 | 0.018 | 212 |
| 7 | THF | 98 | 94.78 | 0.049 | 574 |
| 8 | Acetone | 99 | 96.70 | 0.0279 | 1190 |

EXAMPLE 8

A 50 ml stirred autoclave was charged with the following reactants
p-IBPE: 0.05618 mol
Catalyst having formula I: $1.4125 \times 10^{-4}$ mol
p-toluene sulphonic acid : 0.0163 mol
LiCl: 0.0163 mol
$H_2O$: 60000 ppm
Acetone: 16 ml The contents of the autoclave were flushed with nitrogen and then many times with carbon monoxide. Thereafter, the contents were heated to 115° C. Afer the temperature is attained, the autoclave was pressurized to 1000 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the final reaction mixture analysed by gas chromatography.

The GC analysis showed TOF of 1190 $h^{-1}$ and 99% conversion of p-IBPE with ibuprofen selectivity of 96.7% and n/iso ratio of 0.0279. The product was then isolated after removing the catalyst which was precipitated by adding hexane, and evaporating the solvent.

EXAMPLE 9

A 50 ml stirred autoclave was charged with the following reactants
p-IBPE: 0.05618 mol
Catalyst having formula I: $1.4125 \times 10^{-4}$ mol
p-toluene sulphonic acid : 0.0163 mol
LiCl: 0.0163 mol
$H_2O$: 60000 ppm
Acetone: 16 ml The contents of the autoclave were flushed with nitrogen and then many times with carbon monoxide. Thereafter, the contents were heated to 115° C. After the temperature is attained, the autoclave was pressurized to 500 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the final reaction mixture analysed by gas chromatography.

The GC analysis showed TOF of 550 $h^{-1}$ and 98% conversion of p-IBPE with ibuprofen selectivity of 94% and n/iso ratio of 0.05319. The product was then isolated after removing the catalyst which was precipitated by adding hexane, and evaporating the solvent.

EXAMPLE 10

A 50 ml stirred autoclave was charged with the following reactants
p-IBPE: 0.05618 mol
Catalyst having formula I: $1.4125 \times 10^{-4}$ mol
p-toluene sulphonic acid : 0.0163 mol
LiCl: 0.0163 mol
$H_2O$: 60000 ppm
Acetone: 16 ml The contents of the autoclave were flushed with nitrogen and then many times with carbon monoxide. Thereafter, the contents were heated to 115° C. After the temperature is attained, the autoclave was pressurized to 200 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the final reaction mixture analysed by gas chromatography.

The GC analysis showed TOF of 200 $h^{-1}$ and 98% conversion of p-IBPE with ibuprofen selectivity of 85% and n/iso ratio of 0.16. The product was then isolated after removing the catalyst which was precipitated by adding hexane, and evaporating the solvent.

TABLE 5

| Example | Pressure, psig | p-IBPE conversion, % | Ibuprofen selectivity, % | n/iso | TOF, $h^{-1}$ |
|---|---|---|---|---|---|
| 8 | 1000 | 99 | 96.70 | 0.0279 | 1190 |
| 9 | 500 | 98 | 94.00 | 0.0532 | 550 |
| 10 | 200 | 98 | 85.00 | 0.1600 | 200 |

ADVANTAGES OF THE INVENTION

1. Employment of a novel catalyst under mild reaction conditions in a biphasic as well as homogeneous medium.
2. Provides high reaction rates and high ibuprofen productivity (1.9 Kg/L/h).
3. Provides very high selectivity to Ibuprofen (85 to 98%) even under lower pressures of carbon monoxide (200 to 1000 psig).
4. Provides simple and efficient catalyst recycling.
5. Avoids use of excess ligands.

What is claimed is:

1. A process for the preparation of ibuprofen, which comprises:

reacting para isobutyl phenylethanol (p-IBPE), a halide source, a protonic acid, water and a catalyst having the following formula I:

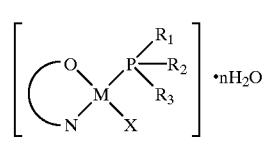

Formula I wherein
M is a group VIII metal,
$R_1$, $R_2$, and $R_3$ are independently selected from the group consisting of hydrogen, alkyl, aryl, arylalkyl, and cycloaliphatic, X is selected from the group consisting of aryl sulphonato, alkylsulphonato, aryl carboxylato, alkyl carboxylato, formato, and halide,

is a semilabile anionic chelating ligand containing a N donor and an O⁻ group, and 1<n<10, said reacting occurring in an organic solvent under constant stirring in a carbon monoxide atmosphere under biphasic or homogeneous conditions, at a temperature ranging between 30 to 130° C., for a period ranging between 0.3 to 6 hours, at pressure ranging between 50 to 1500 psig;

cooling the reaction mixture to ambient temperature;

flushing the reaction vessel with inert gas;

removing the solvent by conventional means;

separating the catalyst; and isolating the product.

2. The process according to claim 1, wherein in said catalyst of formula I, M is palladium or platinum.

3. The process according to claim 1, wherein in said catalyst of formula I, said semilabile anionic chelating ligand is selected from the group consisting of 8-hydroxyquinoline, 2-hydroxypyridine, 2-(2-hydroxyethyl)pyridine, pyridyl-2-carboxylate, piperidyl-2-carboxylate, quinolyl-2-carboxylate, isoquinolyl-1-carboxylate, and isoquinolyl-3-carboxylate.

4. The process according to claim 3, wherein said semilabile anionic chelating ligand is 8-hydroxyquinoline, pyridyl-2-carboxylate, or piperidyl-2-carboxylate.

5. The process according to claim 1, wherein in said catalyst of formula I,

M is palladium, $R_1$, $R_2$, and $R_3$ are phenyl,

X is p-toluenesulphonato (Ots),

n is 3.

6. The process according to claim 1, wherein said halide source is selected from the group consisting of lithium chloride, sodium chloride, potassium chloride, lithium iodide, lithium bromide, sodium bromide, sodium iodide, potassium bromide, potassium iodide, tetrabutyl ammonium chloride, tetrabutyl ammonium bromide, tetrabutyl ammonium iodide, hydrochloric acid, hydrobromic acid, and hydroiodic acid.

7. The process according to claim 1, wherein the protonic acid is selected from the group consisting of hydro halic acids, para toluene sulphonic acid, methane sulphonic acid, trifluoromethane sulphonic acid, formic acid, oxalic acid, acetic acid, and trifluoroacetic acid.

8. The process according to claim 7, wherein said hydro halic acid is selected from the group consisting of hydrochloric acid, hydrobromic acid, and hydroiodic acid.

9. The process according to claim 1, wherein said solvent is an aromatic hydrocarbon, a methyl ethyl ketone, acetone, a cyclic ether, a nitrile, or an amide.

10. The process according to claim 9, wherein said aromatic hydrocarbon is selected from the group consisting of benzene, toluene, and xylene and said cyclic ether is selected from the group consisting of tetrahydrofuran and dioxan.

11. The process according to claim 9, wherein said solvent is said nitrile solvent, said nitrile solvent being acetonitrile.

12. The process according to claim 9, wherein said solvent is said amide solvent, said amide solvent being N-methyl pyrrolidone.

13. The process according to claim 1, wherein 1 mole of catalyst is present for every 50 to 50000 moles of p-IBPE.

14. The process according to claim 13, wherein 1 mole of catalyst is present for every 100 to 6000 moles of p-IBPE.

15. The process according to claim 14, wherein 1 mole of catalyst is present for every 150 to 2000 moles of p-IBPE.

16. The process according to claim 1, wherein 1 gram mole of catalyst is present for every 5 to 500 moles of halide source.

17. The process according to claim 26, wherein 1 gram mole of catalyst is present for every 20 to 300 moles of halide source.

18. The process according to claim 17, wherein 1 gram mole of catalyst is present for every 50 to 150 moles of halide source.

19. The process according to claim 1, wherein 1 gram mole of catalyst is present for every 5 to 500 moles of protonic acid.

20. The process according to claim 19, wherein 1 gram mole of catalyst is present for every 20 to 300 moles of protonic acid.

21. The process according to claim 20, wherein 1 gram mole of catalyst is present for every 50 to 150 moles of protonic acid.

22. The process according to claim 1, wherein said step of reacting is carried out in a stirred reactor in the presence of said catalyst, a suitable solvent, and carbon monoxide.

23. The process according to claim 1, wherein said step of reacting is carried out at a pressure of carbon monoxide up to 50 psig.

24. The process according to claim 1, wherein said step of reacting is carried out in a biphasic or homogeneous medium.

25. The process according to claim 24, wherein said step of reacting is carried out in a homogeneous medium.

26. The process according to claim 1, wherein said catalyst is recycled in the presence of the product.

27. The process according to claim 1, wherein said step of reacting does not require excess ligands.

28. The process according to claim 1, wherein said catalyst is stable in the absence of excess ligands.

* * * * *